United States Patent [19]

Young et al.

[11] 4,170,631
[45] Oct. 9, 1979

[54] CONTROLLED RELEASE FORMULATIONS OF DOUGLAS-FIR BEETLE ANTI-AGGREGATIVE PHEROMONE, 3-METHYL-2-CYCLOHEXEN-1-ONE

[75] Inventors: James W. Young, Palo Alto, Calif.; Malcolm M. Furniss, Moscow, Id.

[73] Assignee: The United States of America as represented by the Secretary of Agriculture, Washington, D.C.

[21] Appl. No.: 929,866

[22] Filed: Jul. 31, 1978

[51] Int. Cl.$^2$ .......................... A01N 5/00; A01N 9/00
[52] U.S. Cl. ........................................ 424/19; 424/22; 424/23; 424/84
[58] Field of Search .................................... 424/19–22, 424/84

[56] References Cited

PUBLICATIONS

Rudinsky J. A., Sartwell, C. Jr., Graves, T. M., Morgan, M. E., Z. Angew, Ent. 75:254–263 (1974) Granular Formulation of Methylcyclohexenone: an Antiaggregative Pheromone of Douglas Fir and Spruce Bark Beetles.

Furniss, M. M., Young, J. W., McGregor, M. D., Livingston, R. L., Hamel, D. R., Canad. Entomol., 109: 1063–1069, Aug. 1977, Effectiveness of Controlled-Release Formulations of MCH for Preventing Douglas-Fir Beetle Infestation in Felled Trees.

Young, J. W., Graves, T. M., Curtis, R., Furniss, M. M., Controlled Release Formulations of Insect Growth Regulators and Pheromones–pp. 184–199, ACS Symposium Series, No. 53, A.C.S. 1977.

*Primary Examiner*—Shep K. Rose
*Attorney, Agent, or Firm*—M. Howard Silverstein; David G. McConnell

[57] ABSTRACT

A method is described for significantly reducing Douglas-fir beetle (*Dendroctonus pseudotsugae* Hopk.) attacks on felled trees, through the use of the Douglas-fir beetle anti-aggregative pheromone, 3-methyl-2-cyclohexen-1-one (MCH), a highly volatile and water soluble material. Controlled release formulations of MCH can prevent the buildup of outbreak population of beetles in susceptible trees. Five controlled-release granular formulations were developed that eluted 3-methyl-2-cyclohexen-1-one (MCH) in the laboratory at a rate $\geq 0.5$ μg/hour for 60 days. The inert components of these formulations consisted either of a wax-coated molecular sieve, polyethylene emulsion-coated ground corncob or dimer acid polyamide beads. These formulations and a liquid standard were applied 9 May (1975) just prior to Douglas-fir beetle (*Dendroctonus pseudotsugae* Hopk.) flight to plots containing single, freshly felled Douglas-fir (*Pseudotsuga menziesii* var. *glauca*) trees. Three months later, infestation by Douglas-fir beetle and other insects was evaluated. All treatments except coated corncobs and certain applications of the molecular sieve significantly reduced Douglas-fir beetle attacks. Douglas-fir beetle brood in three treatments was significantly less than in controls. Abundance of entomophagous insects was proportional to density of host beetle attacks. Douglas-fir beetle attack density was negatively correlated with degree of infestation by the scolytid *Pseudohylesinus nebulosus* (Lec.).

2 Claims, No Drawings

CONTROLLED RELEASE FORMULATIONS OF DOUGLAS-FIR BEETLE ANTI-AGGREGATIVE PHEROMONE, 3-METHYL-2-CYCLOHEXEN-1-ONE

BACKGROUND OF THE INVENTION

1. Field of the Invention:

This invention relates to the control of Douglas-fir beetle (Coleoptera:Scolytidae) infestation in felled trees. More particularly the invention concerns a method for regulating the aggregation of the bark beetle Coleoptera:Scolytidae which exploits controlled release formulation of 3-methyl-2-cyclohexen-1-one (MCH).

2. Description of the Prior Art:

The Douglas-fir bark beetle infests Douglas-fir forests throughout much of the Northwestern United States. Its population occasionally reaches epidemic proportions, especially in trees weakened by windthrow or disease. It was discovered in 1971 (Kinyer, G. W., Fentimon, A. F. Jr., Folty, R. L., Rudinsky, J. A., J. Econ. Ent., (1971), 64, 970.) that the frass of the female Douglas-fir beetle contains a pheromone, 3-methyl-2-cyclohexen-1-one (MCH), which was later shown (Rudinsky, J. A., Furniss, M. M., Kline, L. N., Schmitz, R. F., Can. Entomol., (1972), 104, 815., Furniss, M. M., Kline, L. N., Schmitz, R. F., Rudinsky, J. A., Ann. Entomol. Soc. Amer., (1972), 65, 1227), to have antiaggregative effects on adult beetles. In 1974 it was shown (Furniss, M. M., Daterman, G. E., Kline, L. N., McGregor, M. D., Trostle, G. C., Pettinger, L. F., and Kudinsky, J. A., Can. Entomol., (1974), 106, 381.) that, when released optimally, (i.e. 1 g/acre/day) the pheromone served to reduce beetle attacks upon felled host trees by 96 percent. The pheromone was dispensed in that experiment as neat material from small metal canisters mounted at even spacings around the tree on wooden stakes. This trial served to demonstrate the effectiveness of the treatment, and refined the optimum rate of pheromone release to a narrow range (0.6–1.3 g/acre/day).

SUMMARY OF THE INVENTION

The present invention resides in the discovery of several controlled release formulations of 2 percent 3-methyl-2-cyclohexen-1-one (MCH), a highly volatile and water soluble material, which were effective in reducing Douglas-fir beetle attacks over the course of an entire season. Materials such as MCH which act in the vapor phase, whether insecticides or pheromones, present special problems to the developer of a controlled release formulation. The unique feature of this invention is the discovery of a controlled release formulation of a volatile active ingredient (i.e. MCH).

As reported in 1977 (Young, J. W., Graves, T. M., Curtis, R., and Furniss, M. M. (1977), reprinted from ACS Symposium Series, No. 53. *Controlled Release Pesticides*, p. 195–198, and Furniss, et al., Can. Entomol., (1977), 109: 1063–1069) we developed a release rate method suitable for laboratory screening of formulations which involved the use of tritium-labeled MCH. We disclose the manner in which to produce five formulations which were selected by the screening method for field testing. The details of the field test are also reported.

An object of this invention is to provide a method of releasing a volatile and/or water soluble ingredient over an extended period of time. More particularly, an object of this invention is to provide a method of releasing MCH at a rate of 0.1–1.3 grams/acre/day which will be effective for 30 to 60 days. Another object of this invention is to provide a suitable means for the application of MCH by air. That is, the means of dispersion must enable the MCH to penetrate the forest canopy. Still another object of this invention is to provide a biodegradable, nontoxic controlled release method of controlling Douglas-fir beetle populations at low cost.

DESCRIPTION OF THE PREFERRED EMBODIMENT

The MCH used was supplied by Aldrich Chemical Company (99 pct purity, lot No. 080647). Tritium-labeled MCH (specific activity 70 mc/mmole) was prepared by ICN, Chemical and Radio Isotope Division, Irvine, Calif. This sample was diluted with unlabeled MCH to yield material with a specific activity of 0.005 mc/mmole for studying radiochemical release rate.

Earlier field experiments (Furniss et al., Can. Entomol., (1974), 106: 381–392) established that an optimum MCH release rate was about 1 g/acre/day. We sought a formulation which, when applied at the required dosage (4.1 lb/acre), would maintain this, or a higher, release rate over a 60-day period. Candidate formulations were aged in the laboratory and sampled periodically to measure their release rates. The systems investigated ranged from simple adsorbent clay granulars to complex multibarrier systems.

The physical properties of MCH (solubility in water and vapor pressure) and the use pattern for the material (broadcast application that must reach the ground in dense forest cover) dictated a granular-type formulation. Nearly all of the 70 formulations screened for release rates were of this type.

A quantity of each candidate formulation sufficient to determine release rate at 10 time intervals was placed on steel trays (48 by 20 by 1.5 cm) lined with paper towels. These trays were stacked in a vented fume hood so that a maximum area was exposed to air movement. Airflow through the hood was 150 ft$^3$/min. Trays were repositioned weekly to minimize the effects of variation in turbulence in the hood. Temperature was 72°±2° F.; relative humidity was 40 to 60 percent.

Rates of MCH elution were determined in an apparatus constructed from a 2-liter Erlenmeyer flask. Inlet- and outlet-ports for carrier gas were fitted at the top and bottom, respectively, of the flask. The test formulation was placed in the bottom of the flask, and dry nitrogen carrier gas was passed through the flask. Effluent carrier gas was passed through a glass tube (8 mm i.d.) packed with 0.25 grams of Poropak ® QS (50/80 mesh). Radiolabeled MCH was trapped on this column, and eluted (greater than 99 pct recovery) with 10 milliliters of hexane.

A typical release rate determination involved placing a quantity of formulation containing 14.4 milligrams MCH in the flask, and attaching the trapping column directly to the outlet port of the flask. The carrier gas was passed through the flask at 175 milliliters per minute for 1 hour. The trapping column was then detached and MCH was eluted with 10 milliliters of hexane directly into a 20 milliliter scintillation vial containing 3 milliliters of scintillation fluid. The MCH content was determine by scintillation counting.

Concentrations were chosen so that 100 d/m corresponded to 1.0 µg of MCH. Because background counts were about 10 to 20 d/m, only MCH elution rates of 0.5 µg h and higher could be measured reliably.

Most of the formulations were eliminated from further consideration during the first 14 to 21 days of screening, when the rate of release of MCH fell below 0.5 µg/h. In some cases, MCH was exhausted after an initial period of very high release rate; in others, MCH appeared to be bound to the carrier and never reached a sufficiently high rate of release.

The release rate for each formulation was highly variable from one run to another. This was probably due to difficulties in obtaining representative samples of the aged formulation and to lack of precision in the release rate determination method. However, 12 of the formulations showed promising properties and maintained a rate of release for 30 to 60 days close to or above 1 µg/h in the laboratory. These formulations were evaluated by an independent laboratory (Look, Melvin, *J. Chem. Ecol.*, (1976), 2: 481–486), and after several replicated experiments, five formulations (all containing 2 pct MCH by weight) were selected for evaluation in the field. These formulations were:

Formulation 4

13×molecular sieves (8×12 mesh beads) impregnated with MCH and coated with a 1:1 mixture of paraffin wax (M. P. 62° C.) and polyethylene wax (M. P. 110° C.).

Formulation 8

Ground corncobs (15 to 30 mesh) impregnated with MCH and coated with a polyethylene emulsion. Similar to that used by Rudinsky et al., *Z. ong. Ent.*, (1974), 75: 254–263, but with a different coating and having a longer period of elution in the laboratory.

Formulations 9, 10, and 11

Dimer acid polyamide beads (3 to 8 mesh) of similar molecular weight, impregnated with MCH.

Instructions for the production of formulations 4, 8, 9, 10, and 11 follow.

| Formulation 4 | |
|---|---|
| Ingredients: | Percent by Weight |
| 13 × molecular sieves (8 by 12 mesh beads) | 78.0 |
| Paraffin wax (m. p. ~ 60° C.) | 10.0 |
| Polyethylene wax (AC-680, made by Allied Chemical Company) | 10.0 |
| MCH | 2.0 |
| | 100.0 |

Procedure:

Put sieves in a tumbling type solids mixer and add enough n-pentane to thoroughly moisten the beads. Add MCH while blending. Continue blending in a forced draft until all the solvent has evaporated and the molecular sieves are dry. Place the paraffin and polyethylene waxes in a separate vessel and heat to 130° to 140° C. while mixing to blend the waxes. Add the molecular sieves to the molten wax while mixing. Continue mixing while cooling to allow a wax coating to form on the molecular sieves.

| Formulation 8 | |
|---|---|
| Ingredients: | Percent by Weight |
| Corncob grites (15 to 30 mesh) | 76.0 |
| Propylene glycol | 2.0 |

| Formulation 8 | |
|---|---|
| Ingredients: | Percent by Weight |
| 3-methyl-2-cyclohexen-1-one (MCH) | 2.0 |
| Polyethylene wax emulsion (Polymol C-66 made by the Diamond Shamrock Company) | 20.0 |
| | 100.00 |

Place the corncob grites in a solid mixer equipped with a spray impregnation apparatus. With agitation spray propylene glycol onto the corncob grites to achieve a uniform distribution. Add methylene chloride to the corncob grites until they are thoroughly moistened. Dissolve the MCH in an additional portion of methylene chloride. Add this mixture to the corncob grites with agitation. Continue agitation with mild heating or a forced draft to evaporate all solvent. When dry add the polyethylene wax emulsion with agitation. Continue blending until the corncob grites are uniformly coated.

| Formulations 9, 10, and 11 | |
|---|---|
| Ingredients: | Percent by Weight |
| Dimer acid polyamide beads[1] (3 to 8 mesh) | 97.8 |
| MCH | 2.2 |
| N-pentane[2] | |
| | 115.0 |
| Solvent loss | −15.0 |
| | 100.0 |

[1]In formulation 9 the dimer acid polyamide bead is Milvex 1000, made by the General Mills Chemical Company. In formulation 10 the bead is Milvex 1235, also made by the General Mills Chemical Company. In formulation 11 the bead is Emerey 1553, made by the Emerey Chemical Company.
[2]This figure is approximate. The pentane quantity should be adjusted so that the entire surface of the granules are wet.

Procedure:

Put MCH and pentane into a liquid mixer vessel and stir for 15 minutes or until homogeneous. Put the dimer acid polyamide beads in a solids mixer equipped with a spray impregnation apparatus, and begin mixing. Spray the solution of MCH into the granules while mixing. When the entire solution has been transferred, stop the solids mixer and inspect visually for uniform wetness of the granules. If the solid is not uniformly wet, continue spraying pentane (not containing MCH) until uniform wetting is achieved. Blend for 5 minutes. Apply a slight vacuum and remove pentane while continuing the blending operation. All of the formulations should be packaged in fiber drums with heavy polyethylene bag liners.

As various changes could be made in the above compositions without departing from the scope of the invention, it is intended that all matter contained in the above description shall be interpreted as illustrative and not in a limiting sense. The concentration of MCH need not be limited to 2 percent.

The field test was conducted during 1975 in Meadow Creek drainage 6 miles southwest of Elk River, Clearwater County, Idaho. Elevation was 3,000 feet above sea level. Tree species in the test area were Douglas-fir [*Pseudotsuga menziesii* var. *glauca* (Biessn.) Franco], grand fir [*Abies grandis* (Dougl.) Lindl.], western larch (*Larix occidentalis* Nutt.), and western white pine (*Pinus monticola* Dougl.), in order of abundance.

Thirty live, dominant Douglas-fir trees averaging 24 inches diameter at breast height, 129 feet height, and 103 years age, were felled 21-22 April. Treatments were applied 9 May a few days prior to first Douglas-fir beetle flight.

Treatments consisted of a liquid MCH standard and five granular formulations (table 1). The standard was ca. 300 milligrams MCH in ½-dram vials inside perforated cans set out on stakes at 10 feet spacing. Plots were 30 by 120 feet with one felled tree lengthwise in the middle of each. Plots were no closer than 300 feet apart. The standard and procedure were determined previously (Furniss et al., *Can. Entomol.*, (1974), 106: 381-392). Each granular formulation was broadcast by hand to plots at a rate equal to 4.1 pounds per acre of formulated material or 38 grams per acre actual MCH. Formulation 4 also was applied to the ground at 1/10 the 4.1 pounds per acre ratio. Additionally, Formulation 4 was divided among cans on stakes, as was the liquid standard. Treatments were applied randomly among plots and replicated three times; six control plots were reserved.

Bark was removed from six 1-ft$^2$ sample areas on the sides of felled plot trees at ¼, ½, and ¾ the distance from stump to a 12-inch diameter during 11-15 August. Data were taken on abundance of Douglas-fir beetle attacks and brood; entomophagous insects; and percent of bark infested by associated insects [*Pseudohylesinus nebulosus* (Lec.), *Pissodes fasciatus* Lec., and woodborers (Buprestidae and Corambycidae)]. Air temperatures and precipitation were recorded on two plots by clock-driven instruments throughout the test. Weekly catches of Douglas-fir beetle on 1-ft$^2$ stickly traps baited with frontalin and α-pinene were recorded at two locations approximately ¼ mile from the nearest plots.

Differences in mean numbers of Douglas-fir beetle attacks, brood, and other insects for each treatment were compared to the controls by Student's t-test. Variation resulting from zero counts was overcome by transforming data as follows (Rao, C. R. 1970. *Advanced statistical methods in biometric research*. Hafner, Darien, Conn., p. 209): $y = \sqrt{x + \frac{3}{8}}$. Density of Douglas-fir beetle brood was regressed on number of attacks.

Douglas-fir beetle attacks were observed first on 13 May. Two periods of peak beetle flight were indicated by catches on baited sticky traps. The first peak in June consisted of brood that overwintered as callow adults; the second peak, in July—delayed approximately 2 weeks over earlier years due to cold weather—probably consisted mostly of beetles that had made a previous attack in 1975 and emerged.

Only two trees sustained an increase of two or more attacks on sample areas (6 ft$^2$ per tree) during the second flight. This indicated that (1) control logs and those having ineffective treatments had become unattractive since the first flight; and (2) the MCH treatments that were effective in excluding or lowering beetle attacks during the first flight remained effective during the second flight.

Density of Attack and Brood

Attack density was significantly reduced by five of the MCH treatments; Granules, 4, liquid standard, granules 10, 9, and 11 (see table I). Three of the formulations did not significantly reduce attack density below that of the controls Granules 4, 4$^2$, and 8 (see table I). Two of these were Formulation 4 applied to the ground. Because formulation 4 greatly reduced attacks when applied in cans on stakes, the failures may have been due to leaching of MCH by rain; or the treatment on stakes may have been more effective because it was suspended above ground, thereby enhancing the distribution of the MCH odor. If so, the formulation may be more effective if it is modified to adhere to objects above the ground.

Brood density was significantly reduced by three of the MCH treatments [granules, 4, liquid standard and granules 9 (see table I)], only one of which (Formulation 9) was hand broadcast. During tests with liquid MCH in 1972, attack densities less than 0.7/ft$^2$ generally failed to produce brood (Furniss, et al., *Can. Entomol.*, (1974), 106: 381-392). During the present test, the attack density at which no brood was produced appeared to be lower than the control, and brood tended to increase markedly in numbers with slight increases in numbers of attacks at low attack densities. To be effective in preventing beetle population increases, MCH will have to exclude nearly all attacks from trees such as those in this test.

Table I

Density (no./ft$^2$) of Douglas-fir beetle attacks and brood as a function of MCH

| Treatment | Method[1] | Douglas-fir beetle Attacks | Brood |
|---|---|---|---|
| Granules, 4 | P | 0.1 **[3] | 1 * |
| Liquid standard | P | 0.2 ** | 4 * |
| Granules, 10 | B | 0.3 * | 33 NS |
| Granules, 9 | B | 0.4 * | 7 * |
| Granules, 11 | B | 0.6 * | 26 NS |
| Granules, 4 | B | 1.7 NS | 51 NS |
| Granules, 4[2] | B | 3.5 NS | 42 NS |
| Control | — | 4.8 | 45 |
| Granules, 8 | B | 4.9 NS | 54 NS |

[1] P = in cans on stakes 4 feet above ground, 10 by 10 foot spacing; B = broadcast by hand.
[2] Applied at a rate of 1/10 that of the other granules.
[3] Difference from control is significant at the 0.01 (**) level, 0.05 level (*), or not significant (NS).

Table II

Abundance of entomophagous insects (table II) on samples varied in proportion to numbers of prey brood present. The treatment groups having significantly more entomophagous insects always included the control except for *Temnochila chlorodia* (Mann.), which was too scarce to analyze. A similar correlation was observed in earlier tests (Furniss et al., *Can. Entomol.*, (1974), 106: 381-392). The order of abundance of entomophagous insects by species was comparable to that noted in other years in naturally attacked, untreated trees.

Table II

Density (no./ft$^2$) of entomophagous insects as a function of MCH treatment

| Treatment | Method[1] | Coolides brunneri | Medetera sp. | Cleridae spp. | Temnochila chlorodia |
|---|---|---|---|---|---|
| Granules, 4 | P | 0.2 **[2] | 0.7 ** | 0.3 * | 0 |
| Liquid standard | P | 0.7 ** | 0 ** | 0.1 ** | 0.1 |
| Granules, 10 | B | 0.1 ** | 0.2 ** | 0.1 ** | 0.1 |
| Granules, 9 | B | 0.2 ** | 0.7 ** | 0.2 ** | 0.3 |
| Granules, 11 | B | 0.7 ** | 0.7 ** | 0.1 ** | 0.1 |
| Granules, 4 | B | 4.1 NS | 1.4 * | 0.5 * | 0 |
| Granules, 4[3] | B | 2.4 NS | 0.8 ** | 0.8 * | 0.1 |
| Control | B | 6.3 | 4.5 | 1.4 | 0.1 |

Table II-continued

Density (no./ft²) of entomophagous insects as a function of MCH treatment

| Treatment | Method[1] | Cool- oides brunneri | Mada- tera sp. | Cleridae spp. | Temno- chila chlorodia |
|---|---|---|---|---|---|
| Granules, 8 | B | 5.5 NS | 3.8 NS | 1.1 NS | 0 |

See footnotes on Table I.

The proportions of bark surface infested by other phloeninfesting insects (table III) did not differ by treatment except for the scolytid *Pseudohylesinus nebulosus* (Lec.), which was more abundant in trees treated with Formulation 9. This beetle hibernates overwinter in twigs of Douglas-fir and in duff and takes flight earlier than the Douglas-fir beetle. Douglas-fir beetle attacks were inversely correlated with *P. nebulosus* infestation ($r = -0.41$). For example, one or more Douglas-fir beetle attacks occurred four times more frequently on samples having <50 percent of their surface infested with *P. nebulosus* than on samples having 50 to 90 percent of their surface so infested. The causes of this relationship have not been studied.

The weevil, *Pissodes fasciatus* (Lec.), appeared to be attracted to MCH-treated trees in an earlier study (Furniss et al., 1974), but it infested control trees as well as treated trees in the present test. At the time bark was removed during mid-August, this weevil as well as woodborer larvae had mined only a minor amount of the bark surface (0 pct to 7 pct average), even on samples that were free of scolytids.

Table III

Percent of bark surface infested by other subcortical insects as a function of MCH treatment

| Treatment | Method[1] | Pseudo- losinus nebulosus | Pissodes fasciatus | Woodborers |
|---|---|---|---|---|
| Granules, 4 | P | 35 NS[2] | 0 NS | 2 NS |
| Liquid standard | P | 43 NS | 1 NS | 4 NS |
| Granules, 10 | B | 21 NS | 5 NS | 3 NS |
| Granules, 9 | B | 68 * | 3 NS | 4 NS |
| Granules, 11 | B | 18 NS | 3 NS | 7 NS |
| Granules, 4 | B | 41 NS | 1 NS | 3 NS |
| Granules, 4[3] | B | 42 NS | 2 NS | 4 NS |
| Control | B | 18 | 2 | 2 |
| Granules, 8 | B | 28 NS | 2 NS | 4 NS |

[1]See Table I.
[2]Difference from control is significant at the 0.01 (**), 0.05 level (*), or not significant (NS).
[3]Applied at a rate of 1/10 that of the other granules.

The test demonstrated that several controlled-release formulations containing 2 percent MCH were effective in reducing Douglas-fir beetle attacks. The effective formulations were granules of formulations 4, 10, 9, and 11. However, only formulations 4 and 9 were also effective in decreasing the number of brood. The more effective formulations should be tested against windthrown trees which may differ in their resistance or attractiveness from trees felled by sawing.

Having thus disclosed our invention, we claim:

1. A controlled release repellant composition for Douglas-fir beetles (*Dendroctonus pseudotsugae* Hopk.) which comprises 3-methyl-2-cyclohexen-1-one contained on 13x molecular sieves which have been coated with a 1:1 mixture of paraffin wax and polyethylene wax after impregnation with said 3-methyl-2-cyclohexen-1-one.

2. A controlled release repellant composition for Douglas-fir beetle (*Dendroctonus pseudotsugae* Hopk.) which comprises 3-methyl-2-cyclohexen-1-one contained on dimer acid polyamide beads.

* * * * *